United States Patent
LeGrow et al.

(10) Patent No.: US 6,355,724 B1
(45) Date of Patent: Mar. 12, 2002

(54) COSMETIC COMPOSITIONS CONTAINING SILICONE GEL

(75) Inventors: Gary E. LeGrow, Newberry; W. Leonard Terry, Gainesville, both of FL (US)

(73) Assignee: Clariant LSM (Florida), Inc., Gainesville, FL (US)

( * ) Notice: Subject to any disclaimer, the term of this patent is extended or adjusted under 35 U.S.C. 154(b) by 0 days.

(21) Appl. No.: 09/730,913

(22) Filed: Dec. 6, 2000

(51) Int. Cl.[7] .................................... C08K 5/5419
(52) U.S. Cl. .................... 524/731; 424/401; 528/15
(58) Field of Search ...................... 524/731; 424/401; 528/15

(56) References Cited

U.S. PATENT DOCUMENTS

| | | | |
|---|---|---|---|
| 4,987,169 A | 1/1991 | Kuwata et al. | |
| 5,266,321 A | 11/1993 | Shukuzaki et al. | |
| 5,741,877 A | * 4/1998 | Tiffany | 528/15 |
| 5,760,116 A | 6/1998 | Kilgour | |
| 5,880,210 A | 3/1999 | Schulz, Jr. et al. | |
| 5,919,437 A | * 7/1999 | Lee et al. | 424/68 |
| 5,929,163 A | 7/1999 | Harashima | |
| 6,027,738 A | 2/2000 | Stepniewski et al. | |
| 6,258,365 B1 | * 7/2001 | LeGrow et al. | 424/400 |

* cited by examiner

*Primary Examiner*—Margaret G. Moore
(74) *Attorney, Agent, or Firm*—Hedman & Costigan, P.C.

(57) ABSTRACT

The present invention relates to improved and novel silicone gel compositions comprising at least one low molecular weight volatile organosilicone fluid and at least one elastomer-like silicone composition as matrix. The improved silicone gels of the invention can readily and easily be spread on the skin and possess a desirable dull appearance during application. The silicone films which result after the gel has remained on the skin about 15 to 20 minutes after application, are smooth, slippery, non-tacky and non-shiny with a low detectable residue thereof. Silicone gels applied in alkylsiloxanes exhibit significant improvements over those applied in permethylcyclosiloxanes or in other known media or by known methods.

22 Claims, 1 Drawing Sheet

Sensory Characteristics of Petrolatum vs. Silicone Gel in D5 vs. Silicone Gel in 41M10

COSMETIC COMPOSITIONS CONTAINING SILICONE GEL

FIELD OF THE INVENTION

The present invention relates to silicone gels comprising it least one volatile organosilicone fluid with an elastomeric-like silicone matrix. These compositions immediately after being spread on the skin appear to be dry and impart a non-tacky, silky feel. Following evaporation of the volatile organosilicone fluid, a transparent, water repellent non-extractable organaosilicone film, possessing typical silicone sensory characteristics, remains on the skin. No shiny, oily or greasy characteristics are associated with or occur as a result of using these cosmetic compositions either at application or at any time thereafter.

BACKGROUND OF THE INVENTION

It is well known in the art that volatile, low viscosity organosilicone fluids impart various desirable sensory characteristics to cosmetic formulations. It is also well known in the art that such organosilicone fluids possess very strong spreading characteristics. Consequently, cosmetic formulations containing such volatile organosilicone fluids have a tendency to readily and rapidly spread on the skin beyond the location and areas where they are applied. As a result, there is a great interest and practical objective for developing cosmetic formulations containing volatile low viscosity silicone fluids in an improved physical state which, when spread on the body, particularly the skin, stay in place where spread, and continue to do so, and yet retain their desirable sensory properties. In addition, after the volatile silicone fluid has either subsequently volatilized and/or has been absorbed into the skin, formation of an invisible, continuous water repellent organosilicone film is highly desirable. The compositions having such properties provide unexpected and outstanding usefulness for the cosmetic formulations containing them.

Numerous routes to the preparation of the non-volatile elastomeric-like silicone component of silicone gels have been described. These routes as described in the prior art for example, include (a) hydrolysis and condensation of dimethylhydrogenpolysiloxanes, as described in U.S. Pat. No. 5,266,321, (b) addition polymerization, by hydrosilylation, of vinyl terminated polydimethylsiloxanes by dimethylhydrogen-polysiloxanes as described, in U.S. Pat. Nos. 4,987,169 and 6,027,738, (c) addition polymerization, by hydrosilylation, of a mixture of alpha-olefins and alpha, omega-dienes by Si—H-containing polydimethysiloxanes, as described for example, in U.S. Pat. No. 5,880,210, (d) addition polymerization, by hydrosilylation of vinyl terminated polydimethylsiloxanes by hydrodimethylsiloxanes and hydrodimethylsiloxysilicates, as described in U.S. Pat. No. 5,760,116 and (e) a polyoxyalkylene organopolysiloxane as described, in U.S. Pat. No. 5,929,163.

In all of these references, chemical coupling reactions occur in order to combine functional oligomeric siloxanes to form a single molecule of infinite molecular weight (matrix), thus, leaving no unreacted extractable oligomeric siloxanes in the product. In actual practice; however, there are certain and known reasons whereby not all the functional oligomeric siloxanes do, in fact, become chemically combined to the matrix. While not wishing to be bound by any particular theory, it is believed that these reasons can and may include (a) stoichiometric reactant imbalances of Si—H to Si-Vi or Si-Allyl, leaving, usually, unattached molecules containing Si-Vi or Si-Allyl and (b) steric hindrance of the molecules leaving functional groups unreacted. As a result, any uncombined, non-volatile oligomeric siloxanes are thereafter extractable and will impart the shiny appearance normally associated with silicone oils.

SUMMARY OF THE INVENTION

The present invention relates to novel, clear and colorless cosmetic gel compositions comprising as ingredients thereof, low molecular weight, volatile organosilicone fluids and an elastomeric-like silicone multi-component thickening agent. The low molecular weight volatile organosilicone fluid of the present invention may be chosen from decamethylcyclopentasiloxane, dodecamethylcyclohexasiloxane, and alkylmethylsiloxanes having the general formula RR'Si $(OSiMe_3)_2$, wherein Me is methyl, R is a monovalent aliphatic or aromatic hydrocarbon substituent with from 2 to 8 carbons, and R' is methyl or a $Me_3SiO$ group. The elastomeric-like silicone thickening agent is a silicone matrix produced by dissolving 4 different functional oligomeric silicones, (1) a vinyl terminated polydimethylsiloxane of the general formula $ViMe_2SiO$ $(Me_2SiO)_a SiMe_2Vi$, (2) a hydride terminated polydimethylsiloxane of the general formula $HMe_2Si$ (MeSiO) $_b SiMe_2H$, (3) a vinyl functional $M^{vi}MQ$ organosilicone resin of the general formula $(ViMe_2SiO_{1/2})_c$ $(Me_3SiO_{1/2})_d$ $(SiO_2)$ e, and (4) a hydride functional organosilicone crosslinker of the general formula $HMe_2SiO$ $(HMe_2SiORSiO)_f SiMe_2H$; Wherein Me is Methyl, Vi is Vinyl, M is $Me_3SiO_{1/2}$—, $M^{vi}$ is $ViMe_2SiO_{1/2}$, Q is $SiO_2$, R is a monovalent aliphatic or aromatic hydrocarbon substituent with from 2 to 8 carbons, a may range from 1 to about 200, by may range from 1 to about 200, c and d may range from 3 to about 10, e may range from about 10 to about 20, and f may range from 1 to 3.

The present invention further relates to methods for preparing the gel compositions of the present invention and to their use in cosmetic formulations.

Figure 1:
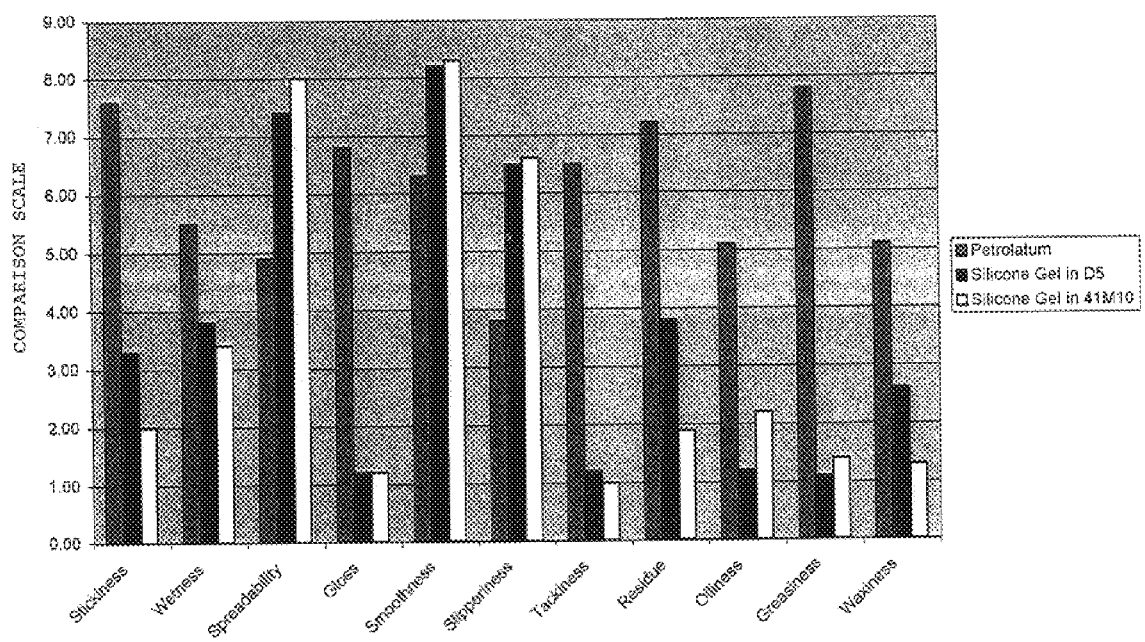
FIG. 1 is a comparison study on a scale basis of petrolatum with silicone gel in D5 and with silicone gel in 41M10.

Various so-called sensory characteristics are compared for the well-known product, petrolatum, and two products of the present invention in known carriers (D5 and 41M10).

DETAILED DESCRIPTION OF THE INVENTION

The improved cosmetic gel compositions are products obtained from the combinations of a first component (a) at least one low molecular weight volatile organosilicone fluid together with a second component (b) at least one elastomeric-like silicone based thickening agent.

The first component (a) may comprise one or more low molecular weight volatile organosilicone fluids which can be one of a number of known siloxanes. These compounds include decamethylcyclopentasiloxane (D5), dodecamethylcyclohexasiloxane (D6), certain alkylmethylsiloxane, of the formula RR'Si $(OSMe_3)_2$ wherein Me is methyl, R is a monovalent aliphatic or aromatic substituent with from 2 to 8 carbon atoms and R' is methyl or a $Me_3SiO$ group and mixtures thereof. Such compounds are available commercially or may be prepared by known methods.

The elastomeric-like silicone thickening agent selected as the second necessary component (b) is a silicone matrix which is produced by hydrosilylating four different structured functional oligomeric silicones to produce the desired resulting cosmetic composition products.

The four structurally different oligomeric silicones which are hydrosilylated to form the thickening agent used are as follows:

1) a vinyl terminated polydimethylsiloxane having the general formula $ViMe_2 SiO(Me_2SiO)_a SiMe_2Vi$,
2) a hydride terminated polydimethylsiloxane having the general formula $HMe_2Si(Me_2SiO)_b SiMe_2H$,
3) a vinyl functional $M^{vi}MQ$ organosilicone resin having the general formula $(ViMe_2SiO_{1/2})_c (Me_3SiO_{1/2})_d (SiO_{1/2})_e$.
4) a hydride functional organosilicone crosslinking agent having the general formula $HMe_2SiO(HMe_2SiORSiO)_f SiMe_2H$.

wherein Me is methyl, Vi is vinyl, M is $Me_3SiO_{1/2}$—, $M^{vi}$ is $ViMe_2SiO_{1/2}$, Q is $SiO_2$, each R is independently a monovalent aliphatic or aromatic hydrocarbon substituent with from 2 to 8 carbons, a may be 1 to about 200, preferably from about 2.5 to about 75, more preferably from about 35 to about 65; b may be 1 to about 200, preferably from about 5 to about 20, more preferably from about 5 to about 15; c and d may be 3 to 10, preferably from about 3 to about 5; e may be about 10 to 20, preferably from about 10 to about 15; and f may be 1 to 3. Each of these four components art known to those skilled in the art, are available commercially or may be produced by methods known in the art.

In preferred embodiments of the present invention, the amounts of the four functional oligomeric silicones may vary as follows; (1) the vinyl terminated polydimethylsiloxane may be employed in amounts ranging from about 35 to about 45 weight percent, preferably 37.5 weight percent; (2) the hydride terminated polydimethylsiloxane may be employed in amounts ranging from about 25 to about 40 weight percent, preferably from about 30 to about 35 weight percent, most preferably 32.5 weight percent; (3) the vinyl functional $M^{vi}MQ$ organosilicone resin maybe employed in amounts ranging from about 20 to about 35 weight percent, preferably 27.5 percent; and (4) the hydride functional crosslinking request may be present in amounts ranging from about 1 to about 10 weight percent, more preferably from about 2.5 to about 5 weight percent.

The ratio of the total Si-Vi equivalents to Si—H equivalents for the four functional oligomeric silicones used should be maintained at 1.05+/−0.05, preferably 1.02+/−0.02, and the resin and crosslinking agent should be adjusted to optimize the sensory properties of the gel during its later use application, and also those properties of the film which result after application of the final product. The molecular structures of the functional ingredients described hereinabove have the Si—H and Si-Vi functionalities only in terminal positions, i.e., only in the form of —$SiMe_2H$ and —$SiMe_2Vi$, in molecules with two or more functional sites. Functionalities of these types generally do not exhibit any steric hindrance difficulties when subjected to hydrosilylation reactions. Consequently, matrices produced with these four ingredient types as defined above generally contain minimal unreacted functionality including both —$SiMe_2H$ and —$SiMe_2Vi$ and minimal amounts of unreacted extractables in the final product. As a further consequence of the absence of residual functionality and extractables, these elastomeric-like matrices exhibit minimal gloss on application to the skin. Furthermore, following, volatilization or absorption of the silicone carrier in the resulting gel system, an elastomeric-like silicone film is formed which is water repellent and is almost invisible following the application of the resulting composition having it incorporated therein.

The hydrosilylation reaction is carried out under conventional hydrosilylation conditions known to those skilled in the art such as on the order of less than about 85° C., preferably at a temperature of from about 25° C. to about 80° C. and in the presence of from about 2 to about 200 ppm, preferably from about 10 ppm to about 50 ppm, of any of the known hydrosilylation catalysts based on the amount of functional components present. Exemplary catalysts are platinum based hydrosilylation catalyst such as chloroplatinicacid or those described in, inter alia, Lamoreaux, U.S. Pat. No. 3,220,972; Karstedt, U.S. Pat. Nos. 3,715,334; 3,775,452 and 3,814,730; Ashby, U.S. Pat. No. 4,421,903; and 4,288,345. Especially preferred are those catalysts commonly referred to as Karstedt's catalysts and Ashby's catalysts. Of course use of other suitable hydrosilylation catalysts known to persons skilled in the art such as those including precious metals such as ruthenium, rhodium, palladium, osmium, and iridium, and complexes of these metals are also contemplated as being within the scope of the present invention.

The method of producing the silicone gels of the present invention proceeds by hydrosilylating the four functional oligomeric silicones with hydrosilyating catalyst in the presence of the low molecular weight volatile organosilicone fluid. Preferably the total amount of hydrosilylation reactants ranges from about 10 to about 20 parts by weight and the total amount of volatile fluid ranges from about 80 to about 90 percent by weight based on the combined weight of hydrosilylation reactants and volatile fluid. The thus formed composition is then preferably sheared in the presence of up to about 100 parts by weight of the same or different volatile organosilcone fluid to form the gels of the present invention.

The compositions of the invention have many advantages over the compositions known and/or are currently in related uses in the cosmetics industry. The gels can also be formulated into cosmetic formulation with the addition of other cosmetic ingredients known to those skilled in the art including non-volatile silicone-aliphatic hydrocarbon hybrid fluids, and organic materials such as long chain aliphatic hydrocarbons and esters. Active ingredients such as strearoxytrimethylsilane can be readily formulated into these mixtures. Other cosmetic additives including perfumes, anti-wrinkle agents, antiperspirant, a humectant, an insect repellent, an odorant, a deodorant, an emollient, an antiseptic, a sunscreen, a cleansing agent, a suitable pharmaceutical, a pigment, a biocide and mixtures of any of the foregoing may also be added.

EXAMPLES

The following Examples are presented solely to illustrate the present invention. They are not however, to be construed to limit in any manner whatsoever, the scope of the invention or the claims thereto.

Example 1

A silicone gel was prepared by reacting 10 ppm of Karstedt's platinum catalyst in 75 g (0.019 mole) of linear $ViMe_2SiO(Me_2SiO)_{51}SiMe_2Vi$, 65 g (0.074 mole) of linear $HMe_2SiO(Me_2SiO)_{10}SiMe_2H$, 55 g (0.039 mole) of $(Me_3SiO_{1/2})_4 (ViMe_2SiO_{1/2})_4 (SiO_2)_{12}$ resin, and 5.0 g (0.0152 mole) of $PhSi(OSiMe_2H)_3$ as the crosslinking agent, at room temperature in 800 g of decamethylcyclopentasiloxane. After 24 hours, a hard gel was formed. Five hundred grams of this gel was then placed in a Waring blender with an additional 500 g of decamethylcyclopentasiloxane. This mixture was sheared by blending at the maximum RPM for about 10 minutes. The resulting liquid was transferred to a glass jar and covered with a tight-fitting screw top cover. After remaining thus at room temperature for about 20 hours, the resulting gel was translucent and had a consistency similar to petrolatum.

Example 2

A silicone gel was prepared using 10 ppm of Karstedt's platinum catalyst in 75 g (0.019 mole) of linear $ViMe_2SiO$ $(Me_2SiO)_{51}SiMe_2Vi$, 65 g (0.074 mole) of linear $HMe_2SiO$ $(Me_3SiO)_{10}$ $SiMe_2H$, 55 g (0.039 mole) of $(Me_3SiO_{1/2})_4$ $(ViMe_2SiO_{1/2})_4(SiO_2)_{12}$ resin, and 5.0 g (0.0152 mole) of $PhSi(OSiMe_2H)_3$ as the crosslinking agent at room temperature in 800 g of 3-n-hexylheptamethyltrisiloxane (SilCare™ 41M10 Hexyl Methicone). After 24 hours, a hard gel was formed. Five hundred grams of this gel was then placed in a Waring blender with an additional 500 g of 3-n-hexylheptamethyltrisiloxane. This mixture was sheared by blending at the maximum RPM for about 10 minutes. The resulting liquid was transferred to a glass jar and covered with a tight-fitting screw top cover. After remaining thus at room temperature for about 20 hours, the resulting gel was transparent and had a consistency similar to petrolatum.

Example 3

A silicone gel was prepared using 10 ppm of Karstedt's platinum catalyst in 75 g (0.019 mole) of linear $ViMe_2SiO$ $(Me_2SiO)_{51}SiMe_2Vi$, 65 g (0.074 mole) of linear $HMe_2SiO$ $(Me_3SiO)_{10}SiMe_2H$, 55 g (0.039 mole) of $(Me_3SiO_{1/2})_4$ $(ViMe_2SiO_{1/2})_4(SiO_2)_{12}$ resin and 5.0 g (0.0152 mole) of $PhSi(OSiMe_2H)_3$ as the crosslinking agent at room temperature in 800 g of n-octyltris (trimethylsiloxy) silane (SilCare™ 3M60 Caprylyl Trimethicone). After 24 hours, a hard gel was formed. Five hundred grams of this gel was then placed in a Waring blender with an additional 500 g of n-octyltris(trimethylsiloxy) silane. An infrared analysis of this mixture confirmed the absence of any absorption at 2100 cm where Si—H is observed. This mixture was sheared by blending at the maximum RPM for about 10 minutes. The resulting liquid was transferred to a glass jar and covered with a tight-fitting screw top cover. After remaining thus at room temperature for about 20 hours, the resulting gel was transparent and had a consistency similar to petrolatum.

Example 4

Following the protocol of ASTM method E1490-92 entitled "Sensory Evaluation of Materials and Products," a Sensory Panel composed of 10 trained volunteers determined the sensory profile of the gels prepared as described in Examples 1 and 2 above and petrolatum. The averaged values for each sensory parameter obtained by the sensory panel are shown and plotted on FIG. 1 described in detail herein above. Of particular note are the lower residue and lower waxiness of the gel film deposited on the skin using 3-n-hexylheptamethyltrisiloxane (SilCare™41M10 Hexyl Methicone) as the carrier versus using decamethylcyclopentasiloxane ($D_5$) as the carrier. There are striking differences between the various sensory characteristics of petrolatum and these silicone gels. These were more or less to be expected from the prior art known. However, and of particular note and importance are the significantly lower gloss and higher spreadability and smoothness values for these silicone gels versus petrolatum.

Comparative Example 1

A silicone gel was prepared using 10 ppm of Karstedt's platinum catalyst in 11.0 g (0.00165 mole) of linear $ViMe_2SiO$ $(Me_2SiO)_{88}SiMe_2Vi$, 22.0 g (0.0156 mole) of $(Me_3SiO_{1/2})_4(ViMe_2SiO_{1/2})_4(SiO_2)_{12}$ resin, and 7.0 g (0.0212 mole) of $PhSi(OSiMe_2H)_3$ crosslinker at room temperature in 360 g of decamethylcyclopentasiloxane. After 24 hours, a soft gel had formed. When this gel was spread on the skin, the film formed was slimy.

Comparative Example 2

A silicone gel was prepared using 10 ppm of Karstedt's platinum catalyst in 16.5 g (0.0025 mole) of linear $ViMe_2SiO$ $(Me_2SiO)_{88}SiMe_2Vi$, 16.5 g (0.0117 mole) of $(Me_3SiO_{1/2})_4$ $(ViMe_2SiO_{1/2})_4$ $(SiO_2)_{12}$ resin, and 7.0 g (0.0152 mole) $(OSiMe_2H)_3$ crosslinker at room temperature in 360 g of 3-n-hexylheptamethyltrisiloxane (SilCare™ 41M10 Hexyl Methicone). After 24 hours, a soft gel had formed. When this gel was spread on the skin, the film formed was shiny and oily. Note: $HMe_2SiO$ $(Me_2SiO)\times SiMe_2H$ is absent from both of the above comparative examples but the stoichiometry was kept at Vi/H≈1.0

Many variations of the present invention will suggest themselves to those of ordinary skill in the art in light of the above-detailed description. For example, gels may be formulated from a mixture of any combination of volatile silicones, volatile alkylsilicone hybrid materials or both and may include volatile and non-volatile organic substances. All such obvious variations are within the full intended scope of the appended claims.

The above-mentioned patents and test methods are hereby incorporated by reference in their entirety.

What is claimed is:

1. A silicone gel composition comprising:
   (a) a low molecular weight volatile organosilicone fluid selected from the group consisting of decamethylcyclopentasiloxane, dodecamethylcyclohexasiloxane, and alkylmethylsiloxanes having the general formula $RR'Si(OSiMe_3)_2$, wherein Me is methyl, and R is a monovalent aliphatic or aromatic hydrocarbon substituent with from 2 to 8 carbon atoms, R' is methyl or $Me_3SiO$—, and combinations thereof, and
   (b) an elastomeric-like silicone matrix produced by platinum catalyzed hydrosilylation curing of four functional oligomeric silicones, having the following compositions:
   (1) a vinyl terminated polydimethylsiloxane having the general formula $ViMe_2SiO(Me_2SiO)_aSiMe_2Vi$,
   (2) a hydride terminated polydimethylsiloxane having the general formula $HMe_2Si(Me_2SiO)_bSiMe_2H$,
   (3) a vinyl functional $M^{vi}MQ$ organosilicone: resin having the general formula $(ViMe_2SiO_{1/2})_c$ $(Me_3SiO_{1/2})_d(SiO_2)_e$, and
   (4) a hydride functional crosslinking agent having the general formula $HMe_2SiO(HMe_2SiORSiO)_f SiMe_2H$; wherein Me is methyl, Vi is vinyl, M is $Me_3SiO_{1/2}$—, $M^{vi}$ is $ViMe_2SiO_{1/2}$, Q is $SiO_2$, each R is independently a monovalent aliphatic or aromatic hydrocarbon substituent having 2 to 8 carbons, a is in the range of 1 to about 200, b is in the range of 1 to about 200, c and d are in the range of 3 to about 10, e is in the range of about 10 to about 20, and f is in the range of 1 to 3.

2. A silicone gel composition according to claim 1, wherein said silicone matrix is in the range of 5 to about 25 weight percent and said volatile organosilicone fluid is in the range of 75 to about 95 weight percent.

3. A silicone gel composition according to claim 1, wherein said silicone matrix is in the range of 10 to about 20 weight percent and said volatile organosilicone fluid is in the range of 80 to about 90 weight percent.

4. A silicone gel composition according to claim 1, wherein said volatile organosilicone fluid is decamethylcyclopentasiloxane.

5. A silicone gel composition according to claim 1, wherein said volatile organosilicone fluid is dodecamethylcyclohexasiloxane.

6. A silicone gel composition according to claim 1, wherein said volatile organosilicone fluid is 3-hexylheptamethyltrisiloxane.

7. A silicone gel composition according to claim 1, wherein said volatile organosilicone fluid is 3-octylheptamethyltrisiloxane.

8. A silicone gel composition according to claim 1, wherein said volatile organosilicone fluid is n-octyltris(trimethylsiloxy)silane.

9. A silicone gel composition according to claim 1, wherein said silicone matrix is produced from
   (1) about 30 to about 45 weight percent of said vinyl terminated polydimethylsiloxane,
   (2) about 25 to about 40 weight percent of said hydride terminated polydimethylsiloxane,
   (3) about 20 to about 35 weight percent of said vinyl functional $M^{vi}MQ$ resin, and
   (4) about 1 to about 10 weight percent of said hydride functional crosslinking reagent.

10. A silicone gel composition according to claim 1, wherein said silicone matrix is produced from
    (1) about 35 to about 40 weight percent of said vinyl terminated polydimethylsiloxane,
    (2) about 30 to about 35 weight percent of said hydride terminated polydimethylsiloxane,
    (3) about 25 to about 30 weight percent of said vinyl functional $M^{vi}MQ$ resin, and
    (4) about 2.5 to about 5.0 weight percent of said hydride functional crosslinking reagent.

11. A silicone gel composition according to claim 10, wherein R is a phenyl substituent, a is in the range of 25 to about 75, b is in the range of 5 to about 20, c and d are in the range of 3 to about 5, e is in the range of 10 to about 15, and f is in the range of 1 to 3.

12. A silicone gel composition according to claim 1, wherein said silicone matrix is produced from
    (1) 37.5 weight percent of said vinyl terminated polydimethylsiloxane,
    (2) 32.5 weight percent of said hydride terminated polydimethylsiloxane,
    (3) 27.5 weight percent of said vinyl functional $M^{vi}MQ$ resin, and
    (4) 2.5 weight percent of said hydride functional crosslinking reagent, and
wherein R is a phenyl substituent, a is in the range of 35 to about 65, b is in the range of 5 to about 15, c and d are in the range of 3 to about 5, e is in the range of 10 to about 15, and f is in the range of 1 to 3.

13. A silicone gel composition according to claim 1, wherein the weight ratio of the total silicon-vinyl equivalency of components (1) plus (3) divided by the total siliconhydride equivalency of components (2) plus (4) is 1.05+/−0.05.

14. A silicone gel composition according to claim 1, where in the weight ratio of the total silicon-vinyl equivalency of components (1) plus (3) divided by the total siliconhydride equivalency of components (2) plus (4) is 1.02+/−0.02.

15. A silicone gel composition according to claim 1, wherein said platinum hydrosilylation catalyst is selected from the group comprising chloroplatinic acid, Karstedt's catalyst and Ashby's catalyst.

16. A silicone gel composition according to claim 1, wherein said platinum hydrosilylation catalyst is present at a concentration of from 10 parts per million, to about 50 ppm, based on the amount of the functional components present.

17. A silicone gel composition according to claim 1, which, when applied to human skin spreads readily and results in a dull, non-glossy finish.

18. A silicone gel composition according to claim 1, which, from 15 to 20 minutes after application to the human skin, results in a smooth, slippery, non-tacky, dull, non-glossy, water repellent silicone coating on the skin so treated.

19. A method of producing a silicone gel composition by
    (a) hydrosilylation curing, with 10 to about 50 ppm of Karstedt's platinum catalyst of 10 to 20 parts by weight of four functional oligomeric silicones combined, said four functional oligomeric silicones having the following compositions:
        (1) a vinyl terminated polydimethylsiloxane having the general formula, $ViMe_2SiO_2(Me_2SiO)_aSiMe_2Vi$,
        (2) a hydride terminated polydimethylsiloxane having the general formula, $HMe_2Si(Me_2SiO)_bSiMe_2H$,
        (3) a vinyl functional $M^{vi}MQ$ resin, having the general formula $(ViMe_2SiO_{1/2})_c(Me_2SiO_{1/2})_d(SiO_2)_e$, and
        (4) a hydride functional crosslinking composition having the general formula $HMe_2SiO(HMe_2SiORSiO)_f SiMe_2H$;
            wherein Me is methyl, Vi is vinyl, M is $Me_3SiO_{1/2}$—, $M^{vi}$ is $Vi Me_2SiO_{1/2}$, Q is $SiO_2$, R is a monovalent aliphatic or aromatic hydrocarbon substituent, a is in the range of 1 to about 200, b is in the range of 1 to about 200, c and d are in the range of 3 to about 10, e is in the range of 10 to about 20, and f is in the range of 1 to 3, in the presence of 80 to 90 parts by weight of a low molecular weight volatile organosilicone fluid selected from the group comprising decamethylcyclopentasiloxane, dodecamethylcyclohexasiloxane, and alkylmethylsiloxanes having the general formula $RR'Si(OSiMe_3)_2$, wherein Me is methyl, and R is a monovalent aliphatic or aromatic hydrocarbon substituent having from 2 to 8 carbon atoms, R' is methyl or $Me_3SiO$—, or any combination thereof, and
    (b) shearing the gel produced in the presence of up to about 100 parts by weight based on the weight of (a) of the same or different additional low molecular weight volatile organosilicone fluid selected from the group comprising decamethylcyclopentasiloxane, dodecamethylcyclohexasiloxane, and alkylmethylsiloxanes having the general formula $RR'Si(OSiMe_3)_2$, wherein Me is methyl, and R is a monovalent aliphatic or aromatic hydrocarbon substituent having from 2 to 8 carbons, R' is methyl or $Me_3SiO$—, or any combination thereof.

20. A method of producing silicone gel composition by
(a) hydrosilylation curing, with 10 ppm of Karstedt's platinum catalyst, of 20 parts by weight of four functional oligomeric silicones combined, said four functional oligomeric silicones having the following compositions:
  (1) 37.5% by weight based on the total weight of said four functional oligomeric silicones of a vinyl terminated polydimethylsiloxane having the general formula $ViMe_2SiO(Me_2SiO)_aSiMe_2Vi$,
  (2) 32.5% by weight based on the total weight of said four functional oligomeric silicones of a hydride terminated polydimethylsiloxane having the general formula $HMe_2Si(Me_2SiO)_bSiMe_2H$,
  (3) 27.5% by weight based on the total weight of said four functional oligomeric silicones of a vinyl functional $M^{vi}MQ$ resin of the general formula $(ViMe_2SiO_{1/2})_c(Me_3SiO_{1/2})_d(SiO_2)_e$, and
  (4) 2.5% by weight based on the total weight of said four functional oligomeric silicones of a hydride functional crosslinking agent having the general formula $HMe_2SiO(HMe_2SiORSiO)_fSiMe_2H$; wherein Me is methyl, Vi is vinyl, M is $Me_3SiO_{1/2}$—, Q is $SiO_2$, R is a monovalent aliphatic or aromatic hydrocarbon substituent., a is in the range of 35 to about 65, b is in the range of 5 to about 15, c and d are in the range of 3 to about 5, e is in the range of 10 to about 15 and f is in the range of 1 to 3, in the presence of 80 parts by weight of a low molecular weight volatile organosilicone fluid selected from the group comprising decamethylcyclopentasiloxane, dodecamethylcyclohexasiloxane and alkylmethylsiloxanes having the general formula $RR'Si(OSiMe_3)_2$, wherein Me is methyl, R is a monovalent aliphatic or aromatic hydrocarbon substituent having from 2 to 8 carbons, and R' is methyl or $Me_3SiO$—, or any combination thereof, and
(b) shearing the gel produced in the presence of 100 parts by weight based on the weight of (a) of the same or different additional low molecular weight organosilicone fluid selected from the group comprising decamethylcyclopentasiloxane, dodecamethylcyclohexasiloxane, and alkylmethylsiloxanes having the general formula $RR'Si(OSiMe_3)_2$, wherein Me is methyl, R is a monovalent aliphatic or aromatic hydrocarbon substituent having from 2 to 8 carbons, and R' is methyl or $Me_3SiO$—, or any combination thereof.

21. A cosmetic formulation comprising a silicone gel composition as defined in claim 1.

22. A cosmetic formulation comprising a silicone gel composition produced by the process of claim 20.

* * * * *